United States Patent
De Magalhaes et al.

(10) Patent No.: US 11,423,281 B2
(45) Date of Patent: Aug. 23, 2022

(54) PERSONALIZED ACTIVITY ADVISER MODEL

(71) Applicant: INTERNATIONAL BUSINESS MACHINES CORPORATION, Armonk, NY (US)

(72) Inventors: Arthur L. De Magalhaes, Markham (CA); Robert K.G. Taniwa, Whitby (CA); Nelson Jean, Markham (CA); Agueda Martinez Hernandez Magro, Zapopan (MX)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 875 days.

(21) Appl. No.: 16/264,832

(22) Filed: Feb. 1, 2019

(65) Prior Publication Data

US 2020/0250508 A1 Aug. 6, 2020

(51) Int. Cl.
*G06N 3/00* (2006.01)
*H04L 67/306* (2022.01)
(Continued)

(52) U.S. Cl.
CPC ....... *G06N 3/006* (2013.01); *G06F 16/24578* (2019.01); *G06F 16/284* (2019.01);
(Continued)

(58) Field of Classification Search
CPC .......... G06N 3/006; G06N 20/00; G06N 5/64; H04L 67/306; G06F 16/284; G06F 16/24578; G16H 10/60
See application file for complete search history.

(56) References Cited

U.S. PATENT DOCUMENTS 5,478,989 A 12/1995 Shepley
6,510,430 B1 1/2003 Oberwager et al.
(Continued)

OTHER PUBLICATIONS

Mel, et al., "The NIST Definition of Cloud Computing," National Institute of Standards and Technology, Information Technology Laboratory, Special Publication 800-145, Sep. 2011 (p. 1-7).
(Continued)

*Primary Examiner* — Etienne P Leroux
(74) *Attorney, Agent, or Firm* — Scott Dobson, Esq.; Kevin P. Radigan, Esq.; Heslin Rothenberg Farley & Mesiti P.C.

(57) ABSTRACT

A processor(s) receives a profile of a user and ranks physical activities in a relational data structure based on the user profile to create a customized relational data structure of ranked physical activities for the user. The relational data structure maps physical activities to one or more associated attributes. An activity adviser model is produced specific to the user via machine learning by obtaining data related to physical activities performed by the user from one or more sensors, and receiving user wellness-related feedback related to the user-performed physical activities. The user wellness-related feedback includes a user ranking of one or more aspects of the user-performed physical activities. The activity adviser model specific to the user is built by using the customized relational data structure, the data and the user wellness-related feedback. The processor(s) uses the activity adviser model to provide an activity-related recommendation to the user.

20 Claims, 10 Drawing Sheets

(51) Int. Cl.
*G06F 16/28* (2019.01)
*G06N 20/00* (2019.01)
*G16H 10/60* (2018.01)
*G06N 5/04* (2006.01)
*G06F 16/2457* (2019.01)

(52) U.S. Cl.
CPC ............... *G06N 5/04* (2013.01); *G06N 20/00* (2019.01); *G16H 10/60* (2018.01); *H04L 67/306* (2013.01)

(56) References Cited

U.S. PATENT DOCUMENTS

| | | | | |
|---|---|---|---|---|
| 6,856,938 | B2* | 2/2005 | Kurtz | G16H 20/60 600/300 |
| 10,772,550 | B2* | 9/2020 | Aceti | A61B 5/15119 |
| 2002/0082144 | A1 | 6/2002 | Pfeffer | |
| 2003/0204412 | A1 | 10/2003 | Brier | |
| 2006/0263750 | A1 | 11/2006 | Gordon | |
| 2007/0059672 | A1 | 3/2007 | Shay | |
| 2013/0209971 | A1* | 8/2013 | Luecke | G09B 19/00 434/127 |
| 2014/0221181 | A1* | 8/2014 | Pickett | G16H 20/30 434/247 |
| 2014/0221784 | A1 | 8/2014 | Pacione et al. | |
| 2015/0118658 | A1* | 4/2015 | Mayou | H04L 67/12 434/127 |
| 2015/0182843 | A1 | 7/2015 | Esposito et al. | |
| 2016/0089077 | A1* | 3/2016 | Geronimo-Button | A61B 5/0205 705/3 |
| 2017/0084196 | A1 | 3/2017 | Nusbaum et al. | |
| 2017/0249599 | A1* | 8/2017 | Barnes | G16H 20/30 |
| 2017/0259121 | A1* | 9/2017 | King | A63B 71/0622 |
| 2018/0301224 | A1* | 10/2018 | Matichuk | A61B 5/0205 |
| 2019/0192043 | A1* | 6/2019 | Leckie | G16H 50/30 |
| 2021/0216560 | A1* | 7/2021 | Power | G06F 16/9032 |

OTHER PUBLICATIONS

International Business Machines Corporation (IBM), "Power ISA™ Version 2.07B," Apr. 9, 2015, (pp. 1-1527).

IBM Publication, "z/Architecture Principles of Operation," IBM® Publication No. SA22-7832-11, 12th Edition, Sep. 2017, pp. 1-1902.

Fahim et al., "Athena: A Personalized Platform to Promote and Active Lifestyle and Wellbeing Based on Physical, Mental and Social Health Perimitives", Sensors, vol. 14, May 2014 (pp. 9313-9329).

Rabbi et al., "My Behavior Automatic Personalized Health Feedback from User Behaviors and Preferences Using Smartphones", UBICOMP '15, Osaka, Japan, Sep. 7-11, 2015 (12 pages).

Smith et al., "Continuously Monitoring the Human Machine", National Geographic Magazine, Jan. 2019 (pp. 56-63).

* cited by examiner

PERSONALIZED ACTIVITY ADVISER MODEL

BACKGROUND

Exercise or physical activity is any bodily activity that enhances or maintains physical fitness and overall health and wellness. Exercise is undertaken for a variety of reasons, including honing athletic skills, strengthening muscles and cardiovascular system, weight loss or maintenance, improving health, and for overall enjoyment. Physical activity is generally grouped into different types, depending on the overall effect on the human body. Aerobic exercise is any physical activity that uses large muscle groups and causes the body to use more oxygen than while resting. The goal of aerobic exercise is to increase cardiovascular endurance. Examples of aerobic exercise include running, swimming, cycling, brisk walking, hiking, playing tennis, etc. Anaerobic exercise is exercise that includes strength and resistance training, and can tone muscles, as well as improve bone strength, balance and coordination. Physical activities can also be directed to flexibility exercises that stretch and lengthen muscles. Activities such as stretching can help to improve joint flexibility and keep muscles limber.

Physical activity can be effected by food consumed before, during and/or after the exercise. Different types of food provide different types of calories including, for instance, fats, alcohol, carbohydrates, and proteins. Different foods or nutritious substances have more or fewer calories packed into the same weight (higher and lower calorie density). Where weight loss is a goal, calorie consumption and physical exercise are interrelated. For instance, to lose a pound, an individual should eat approximately 500 fewer calories per day than expended in metabolism and exercise. The number of calories burned in a day includes basal metabolic rate calories burned to keep the body functioning, plus additional calories burned in physical activity.

The exercise calories burned during cardiovascular activities, such as walking, running, swimming, cycling, etc., depend on the intensity of the exercise, the body weight of the individual, and the amount of time spent exercising. Moderate-intensity exercise, such as a brisk walk, burns fewer calories per minute than a more aggressive-intensity exercise, such as running.

SUMMARY

Certain shortcomings of the prior art are overcome and additional advantages are provided through the provision of a computer-implemented method, which includes receiving, by one or more processors, a profile of a user, and ranking, by the one or more processors, physical activities in a relational data structure based on the user profile to create a customized relational data structure of ranked physical activities for the user. The relational data structure maps physical activities to one or more associated attributes. The method also includes producing, by the one or more processors via machine learning, an activity adviser model specific to the user. The producing includes: obtaining data related to physical activities performed by the user from one or more sensors proximate to the user; receiving user wellness-related feedback related to the user-performed physical activities, the user wellness-related feedback including a user ranking of one or more aspects of the user-performed physical activities; and building the activity adviser model specific to the user using the customized relational data structure, the data and the user wellness-related feedback. The method further includes using, by the one or more processors, the activity-related adviser model specific to the user to provide an activity recommendation to the user.

Computer systems and computer program products relating to one or more aspects are also described and claimed herein. Further, services relating to one or more aspects are also described and may be claimed herein.

Additional features and advantages are realized through the techniques of the present invention. Other embodiments and aspects of the invention are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Aspects of the present invention and certain features, advantages and details thereof, are explained more fully below with reference to the non-limiting example(s) illustrated in the accompanying drawings. Descriptions of well-known materials, systems, devices, processing techniques, etc., are omitted so as to not unnecessarily obscure the invention in detail. It should be understood, however, that the detailed description and the specific example(s), while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure. Note further that numerous inventive aspects and features are disclosed herein, and unless inconsistent, each disclosed aspect or feature is combinable with any other disclosed aspect or feature as desired for a particular application, for instance, for building, using and updating an activity adviser model for personalized health and fitness guidance.

Figure 7:
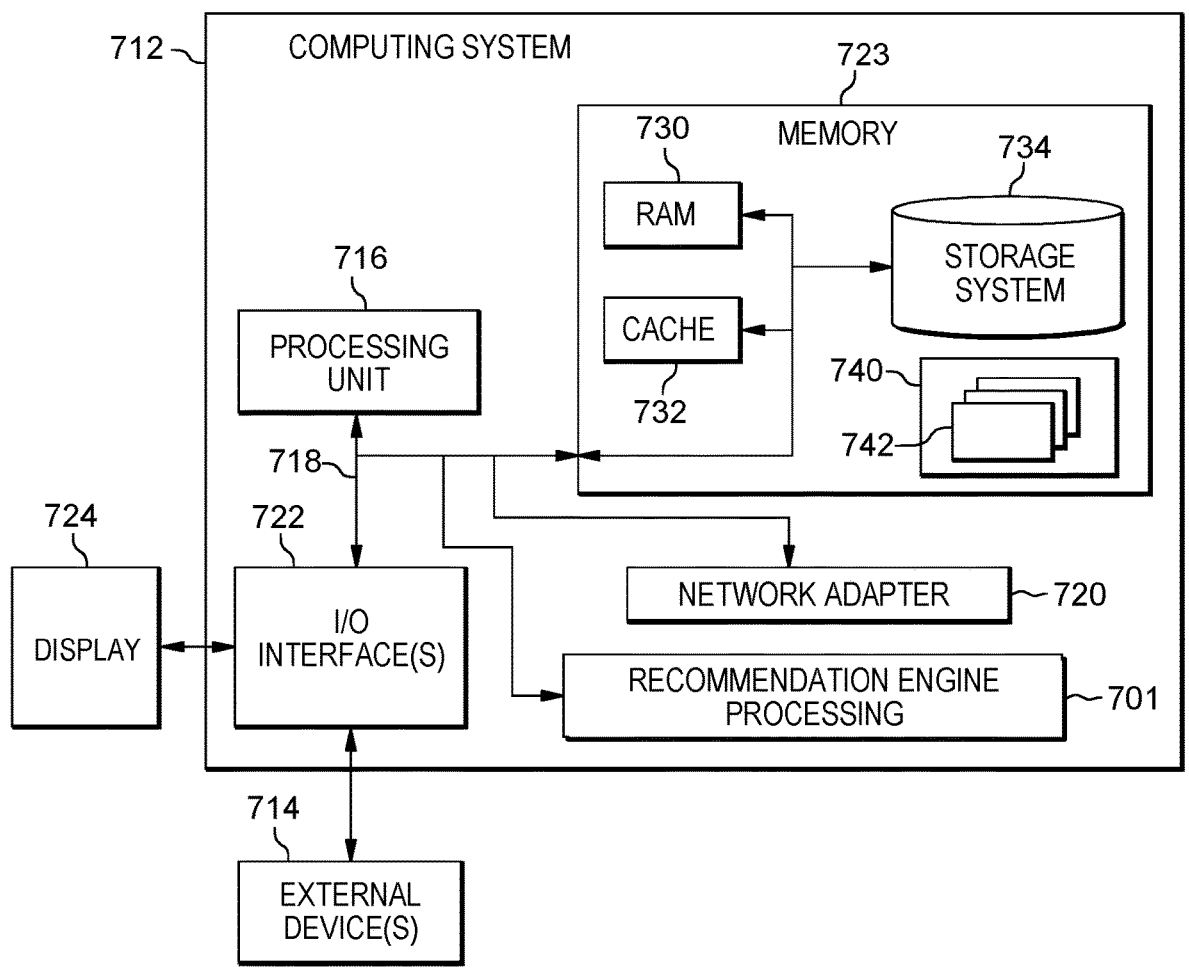
FIG. 7 depicts one embodiment of a computing system which can implement or facilitate implementing recommendation engine processing, including an activity adviser model, in accordance with one or more aspects of the present invention.

As understood by one skilled in the art, program code, as referred to throughout this application, includes both software and hardware. For example, program code in certain embodiments of the present invention includes fixed function hardware, while other embodiments utilize a software-based implementation of the functionality described. Certain embodiments combine both types of program code. One example of program code, also referred to as one or more programs, is depicted in FIG. 7 as program/utility 740, having a set (at least one) of program modules 742, which can be stored in memory 723.

Embodiments of the present invention include a computer-implemented method, a computer program product, and a computing system where program code executing on one or more processors provides a recommendation engine which implements an activity adviser model for personalized fitness and/or health guidance specific to a user. Thus, embodiments of the present invention include program code that provides data to a user to enable the user to better pursue a health or fitness goal (e.g., weight loss, building muscle, etc.), taking into account any health restrictions (e.g., heart rate limits, physical limitations, etc.) of the specific user.

In some embodiments, and activity adviser model, or more generally, recommendation engine, is created, which includes building, by one or more processors, a relational data structure that maps physical activities to one or more associated attributes. The building of the relational data structure is based on a body of domain knowledge obtained via a plurality of sources, such as a plurality of online sources. This building can include cognitively analyzing, via machine learning, the body of domain knowledge obtained from the plurality of online sources to build a relational data structure mapping physical activities to one or more selected attributes, such as average heart rate of individuals during the physical activity, calories typically used by individuals in performing the physical activity, food consumed by individuals in association with a particular physical activity either before, during, or after the physical activity that may yield best results, etc.

In one or more embodiments, one or more processors receive a health and/or goal profile of the user, and the one or more processors rank physical activities in the relational data structure based on the user profile to create a customized relational data structure of ranked physical activities for the user. As noted, the relational data structure maps physical activities to one or more associated attributes. By way of example, the user profile can include data on one or more user inputs, such as user fitness goals and/or user health goals or restrictions.

In some embodiments, the program code executing on one or more processors produces the activity adviser model specific to the user, or more generally, recommendation engine, with the ability to learn about an individual's physical activity patterns, and provide a fitness-related recommendation, either reactively or proactively, based on various inputs, such as diet, calorie consumption, fitness, health goals, etc., as well as any health restrictions. In some embodiments of the present invention, the program code uses data from one or more sensors associated with the individual, or computing devices of the individual (e.g., with which the user interacts), including but not limited to Internet of Thing (IoT) devices, and mobile devices, to obtain data related to physical activities performed by the user (e.g., performed exercises, such as walking, running, swimming, biking, strength training, etc.).

Further, in some embodiments of the present invention, program code receives user wellness-related feedback related to the physical activities performed, with the user wellness-related feedback including a user-perceived ranking of one or more aspects of the user-performed physical activities (e.g., length of activity, effort during the activity, enjoyment of the activity, ease of start of the activity, etc.).

In one or more embodiments, the program code running on the one or more processors builds the activity adviser model specific to the user using the customized relational data structure, the data collected via the one or more sensors associated with the individual, as well as the user wellness-related feedback provided by the user, including the ranking of the one or more aspects of the user-performed physical activities. By way of example, the algorithms and/or data structures constituting the activity adviser model are configured via machine learning to the specific user based on, for instance, the user's profile, the collected data on the physical activities performed by the specific user, as well as the user wellness-related feedback provided by the user concerning the user-performed physical activities. In this manner, for instance, the program code constructs and/or prioritizes recommendations for physical activities, as well as, for instance, food/calorie consumption that may assist the user in performing the physical activity and/or reaching a user-specified goal.

In some embodiments, the activity adviser model, or more generally, recommendation engine, is used to provide an activity-related recommendation to the user, via, for instance, one or more devices, such as one or more user devices. For instance, the activity-related recommendation can be one or more preferred physical activities to be performed by the user based on a food choice of the user, or one or more preferred foods to be consumed by the user based on a physical activity choice of the user.

In some embodiments, the activity adviser model specific to the user relates, at least in part, ranked physical activities of the user to recommended food consumption for the ranked physical activities obtained from, for instance, the general body of domain knowledge. Further, the user wellness-related feedback can include user-provided data on food consumed by the user in association with a physical activity of the physical activities performed by the user. In one or more embodiments, the data obtained related to the physical activities performed by the user can be user physiological data, user heart rate, user blood pressure, user oxygen saturation, blood sugar levels, user temperature, and can be obtained before, during, and/or after one or more of the physical activities. Further, in some embodiments, the user wellness-related feedback obtained can include a user ranking of one or more aspects of a physical activity based on the user's perception of the activity. The user ranking of aspect(s) can include at least some of a user ranking of a length of a physical activity, a user ranking of how the user feels during the physical activity, a user ranking of user enjoyment of the physical activity, a user ranking of ease of the physical activity to the user, etc.

In some embodiments, the activity adviser model, or more generally, recommendation engine, is configured for dynamic updating over time, based on new data. The new data can be one or more updates to the body of domain knowledge obtained from the plurality of sources, and/or further data obtained related to further physical activities performed by the user from, for instance, one or more sensors proximate to the user, as well as further user wellness-related feedback received from the user related to, for instance, the further user-performed physical activities.

By way of example, the dynamically updating of the activity adviser model specific to the user can be based, at least in part, on additional user wellness-related feedback related to the user performing one or more physical activities of the ranked physical activities. The additional user wellness-related feedback can include, at least in part, a re-ranking of one or more aspects of the user-performed physical activities.

Figure 2:
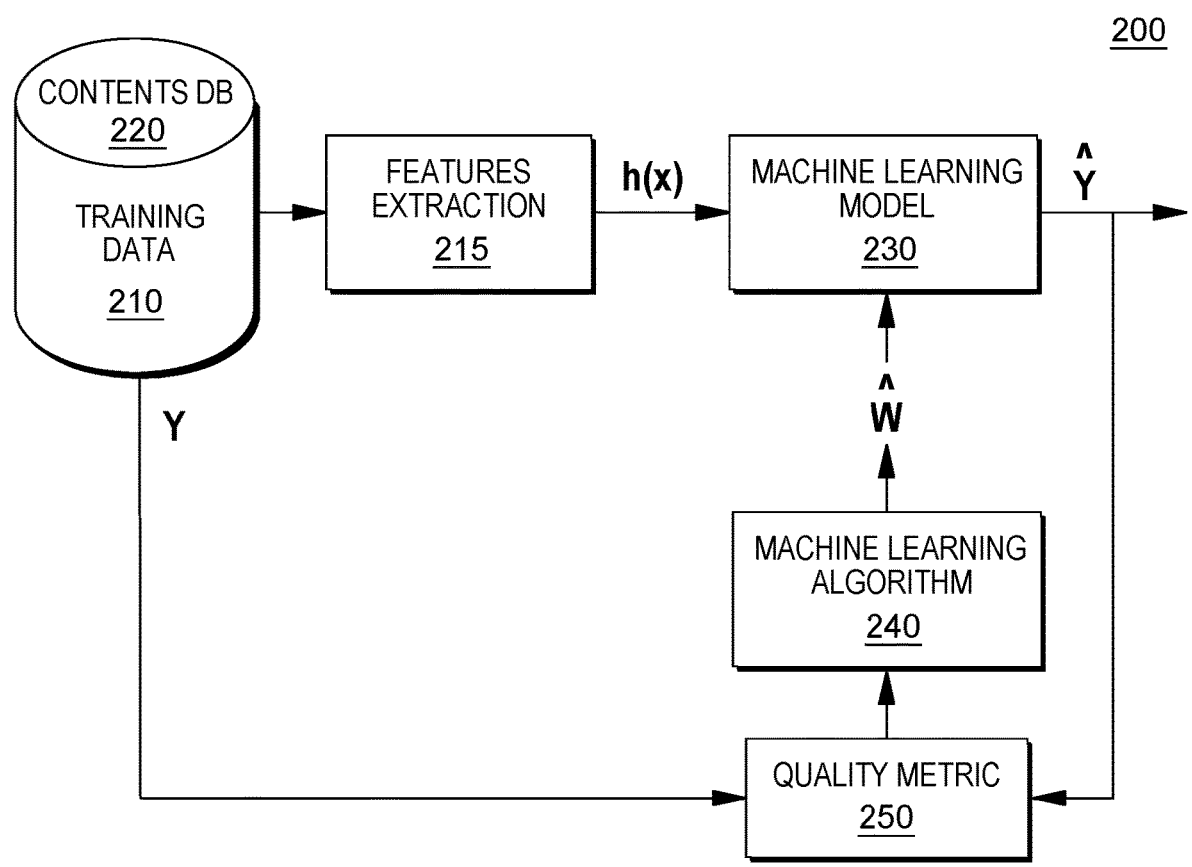
FIG. 2 depicts one embodiment of a workflow illustrating certain aspects of an embodiment, in accordance with the present invention.

In some embodiments of the present invention, the program code generates the activity adviser model specific to the user through machine learning. FIG. 2, which is described further herein, illustrates a machine learning process utilized by program code in embodiments of the present invention to formulate an adviser model for a particular user. Through machine learning, program code executing on one or more processors, in some embodiments of the present invention, cognitively analyzes domain-accessible data to extract, for instance, possible physical activities and recommended food consumption for inclusion in the model. The program code, through machine learning, can access domain knowledge for health, nutrition and exercise, such as from one or more exercise training applications providing available community data on particular exercises, as well as related domain knowledge, including from books, journals, articles, etc., as well as any other computing environment accessible data. The program code, through machine learning, can compare attributes of each exercise found in the body of knowledge against the user profile of the particular individual. In some embodiments, the program code, through machine learning, maintains a data structure of ranked physical activities for the user based, at least in part, on the data and the user's wellness-related feedback, as well as a customized recommendation data structure for the user correlating the ranked physical activities to recommended food consumption for, e.g., each of the ranked physical activities. The program code, through machine learning, identifies patterns with and routines shared from one or more social communities or applications, and available domain knowledge (e.g., training applications, journals, etc.), and uses this information to enhance the adviser model.

Embodiments of the present invention are inextricably tied to computing and provide significantly more than existing technological approaches to providing nutrition and fitness information, and well as to nutrition and fitness tracking. Embodiments of the present invention enable program code executing on one or more processors to exploit the interconnectivity of various systems, as well as utilize various computing-centric data analysis and handling techniques, in order to generate a continuously updated, activity adviser model specific to a user. The program code applies the model in order to provide customized fitness and/or health recommendations identified by the program code. Both the interconnectivity of the computing systems utilized and the computing-centric data processing techniques utilized by the program code enable various aspects of the present invention. Further, embodiments of the present invention provide significantly more functionality than existing approaches to ascertaining nutritional and fitness data recommendations because, in embodiments of the present invention, the program code provides, in certain embodiments, predictive fitness and health recommendations to the user of a physical activity to be performed, for instance, based on a user-selected food, or of a food to be consumed by the user based on a user-selected physical activity using a user-specific activity adviser model.

Some existing approaches generally track nutrition consumed by an individual, or metrics of an individual's fitness, including tracking a particular activity performed by an individual. However, in embodiments of the present invention, the program code provides significantly more functionality, including but not limited to: (1) the program code builds a relational data structure that maps physical activities to one or more associated attributes, where the building is based on a body of domain knowledge obtained from a plurality of sources; (2) the program code receives a profile of the user, and ranks physical activities in the relational data structure based on the user profile to create a customized relational data structure; and (3) the program code produces an activity adviser model specific to the user.

Producing the activity advisor model for the user includes the program code determining a plurality of physical activities performed by a user by obtaining data related to physical activities performed by the user from one or more sensors proximate to the user. The program code also receives user wellness-related feedback related to the physical activities, where the user wellness-related feedback includes a ranking of one or more aspects of the physical activities, and the program code builds the activity adviser model specific to the user using the customized relational data structure, the data and the user wellness-related feedback. In addition, the program code uses the activity adviser model to provide activity-related recommendations to the user, either reactively or proactively.

Figure 1:
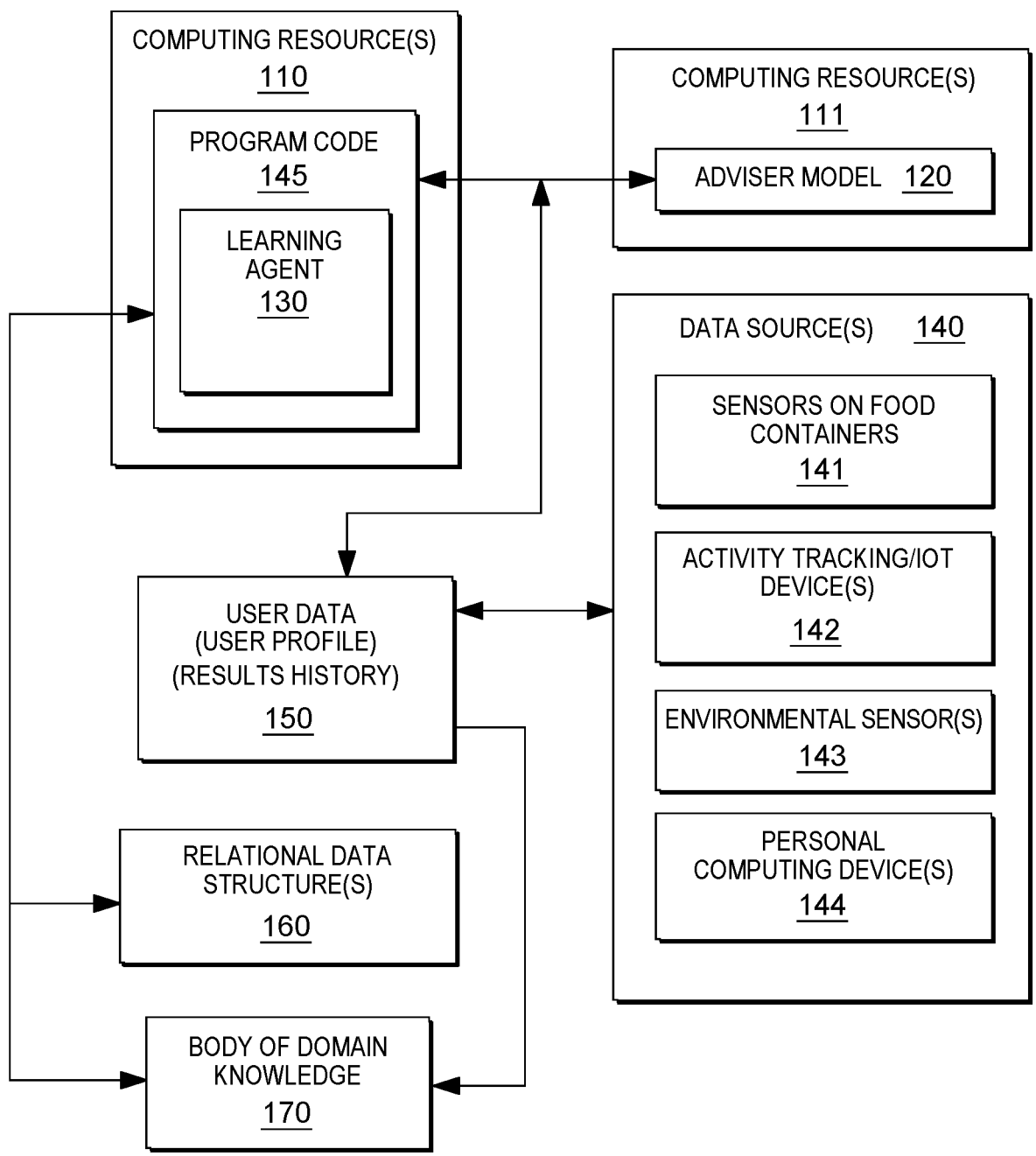
FIG. 1 is an illustration of a technical environment into which various aspects of an embodiment can be implemented, in accordance with the present invention.

FIG. 1 depicts one embodiment of an environment 100 into which various aspects of some embodiments of the present invention can be implemented. Environment 100 includes computing devices, including one or more computing resources 110 that execute program code 145 that generates or updates a model 120, based on machine learning (e.g., via cognitive and/or learning agent 130), and utilizes model 120 to identify a fitness recommendation for a particular user of a physical activity to be performed based on, for instance, a user-selected food, such as a user-consumed food, or of a food to be consumed by the user based on a user-selected physical activity. For illustrative purposes only, model 120 is depicted in FIG. 1 as being housed on a separate computing resource 111 from the one or more computing resources 110 that execute program code 145. This is a non-limiting example of an implementation, and the program code 145 and the model 120 can also share a computing resource. Likewise, in the illustrated embodiment, the program code 145 is illustrated as including the learning agent 130. However, various modules of the program code 145 can be executed on varied resources and various embodiments of the present invention, thus, the learning agent 130 and the program code 145 can be separate modules.

In embodiments of the present invention, program code 145 utilizes various user data 150 from various sensors, activity trackers, cameras (or other activity-capture or data-capture, etc., devices), biometric feedback, user device inputs, such as fitness goals, and/or health restrictions, to identify a fitness or activity recommendation for the user. By way of example only, user data 150 can be provided from various data sources 140, including but not limited to, for instance, sensors on food containers 141, continuous monitoring systems, such as activity tracking devices or Internet of Thing (IoT) devices 142, environmental sensors 143 in various environments, including sensors within a workout environment within which the individual is exercising, as well as personal computing devices 144, utilized by the user and/or proximate to the user.

As noted, user data 150 can include, for instance, food-related data collected from one or more sensors, devices, monitoring systems, etc., and/or provided by the user to program code 145 (e.g., labels and/or sensors on containers 141), as well as activity tracking, IoT devices, etc., 142, and other environmental (e.g., environmental sensors 143), and/or personal computing devices (e.g., personal computing devices 144) for imputing activity-related goals, health restrictions, etc. As understood by one skilled in the art, the Internet of Things (IoT) is a system of interrelated computing devices, mechanical and digital machines, and objects that can be provided with unique identifiers and the ability to transfer data over a network without requiring human-to-human or human-to-computer interaction. These communications can be enabled by smart sensors, which include, but are not limited to, both active and passive radio-frequency identification (RFID) tags, which utilize electromagnetic fields to identify automatically and to track tags associated with objects and/or people. Smart sensors, such as RFID tags, can track environmental factors related to a user or object, including but not limited to, temperature and humidity. The smart sensors can be utilized to measure temperature, humidity, vibrations, motions, light, pressure and/or altitude, etc. IoT devices 142 can also include individual activity and fitness trackers, which include (wearable) devices or applications that include smart sensors for monitoring and tracking fitness-related metrics, such as distance walked or run, calorie consumption, heart rate, quality of sleep, and include smart watches that are synched to a computer or smart phone for long-term data tracking. In some embodiments of the present invention, program code 145 executed by the one or more computing resources 110 utilizes IoT devices 142, such as personal fitness trackers and other types of motion trackers, to obtain data related to physical activities performed by a user. IoT devices also includes smart devices, digital assistants, etc., which are also examples of environmental sensors 143. Because the smart sensors in IoT devices 142 carry unique identifiers, a computing system that communicates with a given sensor can identify the source of the information. Within the IoT, various devices can communicate with each other and can access data from sources available over various communication networks, including the Internet. Thus, program code 145 in some embodiments of the present invention, utilizes data obtained from various devices to generate or update the adviser model 120 utilized by the program code 145 to generate a fitness recommendation for a user.

In some embodiments of the present invention, user data 150 includes biometric and/or physiological data from monitoring of the user during physical activity and includes, but is not limited to, cardiovascular measurements, heart rate, blood pressure, blood oxygen saturation, body movement data (activity-type data), body temperature, and environmental conditions of the environment of the physical activity (e.g., temperature and humidity).

The program code 145 can update adviser model 120 in real time, upon receipt of user data 150, including any sensor data that deviates from adviser model 120. Program code 145 or learning agent 130 utilizes this user data 150 to continually learn and update the patterns that form the adviser model 120. An event that would trigger the program code 145 to update the adviser model 120 in real time would be user data 150 indicating that an individual is performing a new physical activity, has re-ranked one or more aspects of a user-performed physical activity, has provided further feedback on food consumption in association with a physical activity, etc.

As noted, in embodiments of the present invention, program code 145 on one or more computing resources 110 determines, either proactively or reactively, a customized activity-related (or fitness) recommendation to a user. Program code 145 makes this recommendation based on the customized activity adviser model built for the user correlating, for instance, ranked physical activities to recommended food consumption for each of the ranked physical activities, as well as other attributes associated with the activity. The process includes cognitively analyzing domain-accessible data (such as general exercise/food data) accessible to program code 145, for instance, across a network, such as the Internet. The program code 145 utilizes this body of domain knowledge 170 obtained, along with the user data 150, to tailor the model specific to the user. For example, program code 145 with learning agent 130 can incorporate data from one or more online accessible exercise-related sources and/or accessible food-related sources to, for instance, extract recommended food consumption for various activities recommended and/or performed by a community of other individuals. For example, in some embodiments of the present invention, program code 145 extracts recommended food consumption for a particular activity by utilizing a cognitive analysis agent (such as IBM Watson®) to analyze any relevant data and extract therefrom a recommendation for a particular food type and amount based on a particular physical activity. Note in this regard that the particular type of food, as well as the amount, can vary individual-to-individual, as well as physical activity-to-physical activity based, for instance, on fitness goals and general health of the user. In some embodiments, program code 145 executing on one or more computing resources 110 applies machine learning algorithms to generate and train adviser model 120, which the program code 145 then utilizes to generate a fitness recommendation for the user based, for instance, on a chosen physical activity or a chosen food. In this initialization or learning stage, program code 145 trains the algorithms, based on patterns, health, goals, etc., of a given user. As part of this, program code 145 can construct one or more relational data structures 160 that map physical activities to one or more associated attributes. The relational data structure(s) 160 can be built or ascertained based on the body of domain knowledge 170 obtained from a plurality of sources, such as described herein. Note in this regard that the user-performed physical activities documented in the user data 150 can also form a part of the body of domain knowledge 170, and can increase the body of domain knowledge 170 over time as the user performs additional physical activities.

FIG. 2 is an example of a machine learning training system 200 that can be utilized to perform cognitive analysis of various inputs, including the user data 150, and body of domain knowledge 170 of FIG. 1. As noted, training data utilized to train the model in embodiments of the present invention includes historical data personalized to the individual user, including but not limited to: (1) user data 150 (e.g., physiological data from user monitoring, including cardiovascular measures, such as heart rate, blood pressure, blood oxygen saturation, rest versus activity data from body movement and body position, body temperature, ambient conditions, etc.); (2) fitness goals of the user; and/or (3) health restrictions of the user.

The program code in embodiments of the present invention performs a cognitive analysis to generate data structures, including algorithms utilized by the program code to generate and provide an individualized fitness recommendation to a user. Machine learning (ML) solves problems that cannot be solved by numerical means alone. In this ML-based example, program code extracts various features/attributes 215 from training data 210 (e.g., data collected from various data sources relevant to the individual and general data), which can be resident in one or more databases 220, including individual-related data and general data. The features are utilized to develop a predictor function, h(x), also referred to as a hypothesis, which the program code utilizes as a machine learning model 230. In identifying a fitness recommendation for a user, the program code can utilize various techniques to select features (elements, patterns, attributes, etc.) including, but not limited to, diffusion mapping, principal component analysis, recursive feature elimination (a brute force approach to selecting features), and/or a Random Forrest to select, for instance, the attributes related to various effects of food consumption on physical activity experienced by other individuals, as well as other relationships associated with a physical activity. The program code can utilize a machine learning algorithm 240 to train the machine learning model 230 (e.g., the algorithms utilized by the program code), including providing rankings or weights for extracted data or conclusions, so that the program code can train the predictor or recommendation functions to include the machine learning model 230. The conclusions can be evaluated by a quality metric 250. By selecting an appropriate set of training data 210, the program code trains the machine learning model 230 to identify and weight various attributes (e.g., features, patterns) that correlate (for example) physical activities and various results experienced in consuming foods in connection with the activities.

Returning to FIG. 1, the adviser model 120 generated by program code 145 can be self-learning, as the program code 145 updates the model 120 based on feedback received from user data 150 during the operational phase; that is, after the learning phase, related to monitoring the individual. For example, when program code 145 determines that an individual is performing a new physical activity, program code 145 utilizes learning agent 130 to update adviser model 120 to reflect the new physical activity, in order to improve future fitness recommendations to the user. Program code 145 includes a learning agent 130 which cognitively analyzes any new data deviating from the model data, and adjusts the model 120 to improve the model moving forward.

In some embodiments of the present invention, program code 145 executing on one or more computing resources 110 utilizes existing cognitive analysis tools or agents to create, and tune, model 120, based, for instance, on data obtained from the various data sources, including user data 150, relational data structure(s) 160, including any customized relational data structure(s) as described herein, and the body of domain knowledge 170. Some embodiments of the present invention utilize IBM Watson® as learning agent 130 (i.e., as a cognitive agent). IBM Watson® is a registered trademark of International Business Machines Corporation, Armonk, N.Y., USA. In embodiments of the present invention, program code 145 interfaces with IBM Watson® application programming interfaces (APIs) to perform a cognitive analysis of obtained data. In some embodiments of the present invention, program code 145 interfaces with the application programming interfaces (APIs) that are part of a known cognitive agent, such as the IBM Watson® Application Program Interface (API), a product of International Business Machines Corporation, to determine impacts of data on the adviser model for the individual, and to update the model, accordingly.

In some embodiments of the present invention, certain of the APIs of the IBM Watson® API include a cognitive agent (e.g., learning agent 130) that includes one or more programs, including, but not limited to, natural language classifiers, Retrieve and Rank (i.e., a service available through the IBM Watson® Developer Cloud that can surface the most relevant information from a collection of documents), concepts/visual insights, trade-off analytics, document conversion, and/or relationship extraction. In an embodiment of the present invention, one or more programs to analyze the data obtained by the program code 145 across various sources utilizing one or more of a natural language classifier, Retrieve and Rank APIs, and trade-off analytics APIs.

The program code 145 can provide predictions or recommendations for a given individual as varying values. In some embodiments of the present invention, program code 145 (or recommendation engine) can provide a specific fitness recommendation to the individual, which represents whether the recommendation is predicted to provide the desired effect. In other embodiments of the present invention, program code 145 can provide the user with an indicator of one or more of: (1) a probability that the recommendation will achieve the desired effect; and/or (2) a confidence level related to the prediction.

In some embodiments of the present invention, program code 145 utilizes a neural network to analyze collected data relative to a user to generate adviser model 120 utilized to generate a fitness or activity-related recommendation for the individual. Neural networks are a programming paradigm which enable a computer to learn from observational data, in this case, sensor data, fitness goals, health restrictions, body of knowledge, etc. This learning is referred to as deep learning, which is a set of techniques for learning in neural networks. Neural networks, including modular neural networks, are capable of pattern (e.g., state) recognition with speed, accuracy, and efficiency, in situations where data sets are multiple and expansive, including across a distributed network, including but not limited to, cloud computing systems. Modern neural networks are non-linear statistical data modeling tools. They are usually used to model complex relationships between inputs and outputs or to identify patterns (e.g., states) in data (i.e., neural networks are non-linear statistical data modeling or decision making tools). In general, program code 145 utilizing neural networks can model complex relationships between inputs and outputs and identify patterns in data. Because of the speed and efficiency of neural networks, especially when parsing multiple complex data sets, neural networks and deep learning provide solutions to many problems in multiple-source processing, which the program code 145 in embodiments of the present invention accomplishes when obtaining data and building a model for providing fitness or activity-related recommendations for a particular user.

Figure 3:
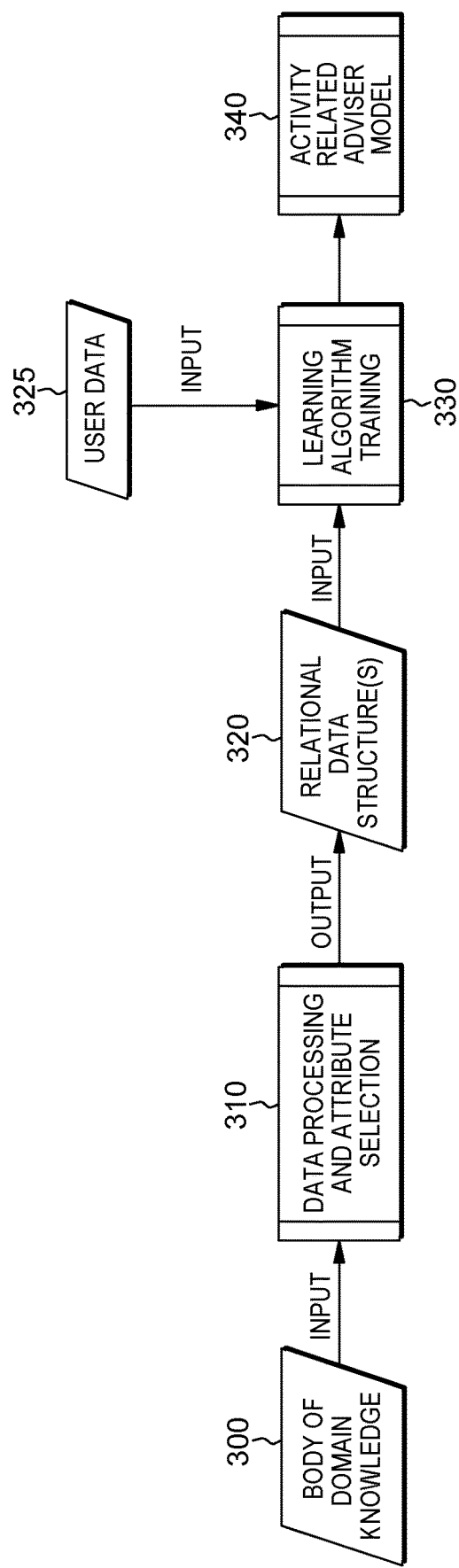
FIG. 3 depicts one embodiment of a machine learning model (or activity adviser model) creation process, in accordance with one or more aspects of the present invention.

FIG. 3 depicts a further overview of a machine learning model creation process, in accordance with certain aspects described herein. As noted, the process receives or ascertains as input a body of domain knowledge 300, such as a body of domain knowledge obtained from a plurality of sources, including sources that describe physical activities, associated attributes, and/or food-related information relevant to the physical activities. Note that food is used generally herein to refer to any substance (including liquid) consumed to provide nutritional support, and in particular, available food-related data relevant to physical activity, such as food-related data relevant to performing a particular physical activity, including relevant to effort level and duration. As noted, the body of domain knowledge can reference a variety of sources, including available training application sources, each from a community of individuals, related knowledge from books, journals, articles, etc., as well as information available from one or more other activity adviser models.

The body of domain knowledge 300 is input to the program code which processes the information and selects attributes 310 to produce, in one or more embodiments, a relational data structure(s) 320 that maps physical activities to one or more associated attributes. The relational data structure(s) 320 and the user data 325 are input to learning algorithm training 330, in which a learning algorithm uses the relational data structure(s) 320 and user data 325 to produce an activity adviser model 340 that is configured/ trained to, for instance, predict or provide recommendations to a particular user based on knowledge created from the relational data structure(s) 320 and the user data 325.

Figure 4A:
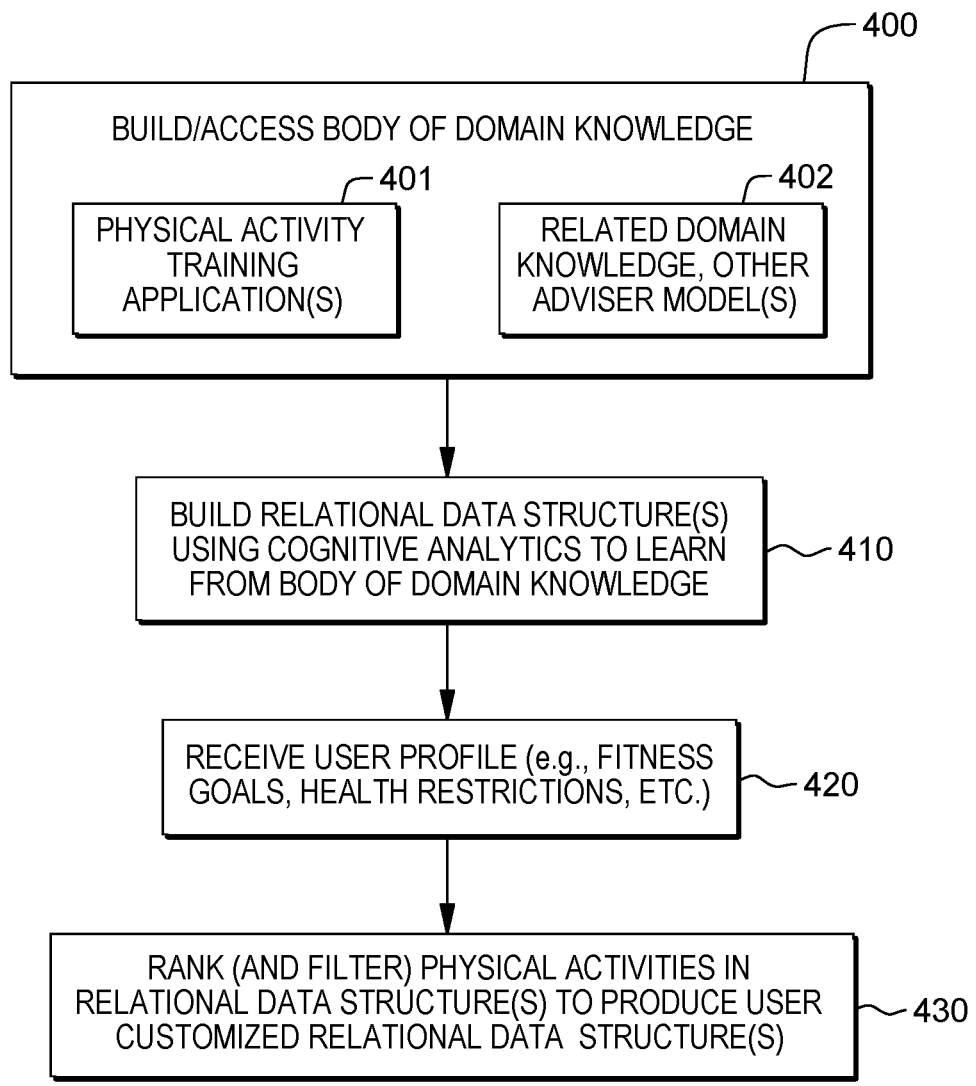
FIGS. 4A & 4B depict a more detailed embodiment of an activity adviser model creation and use process, in accordance with one or more aspects of the present invention.
Figure 4B:
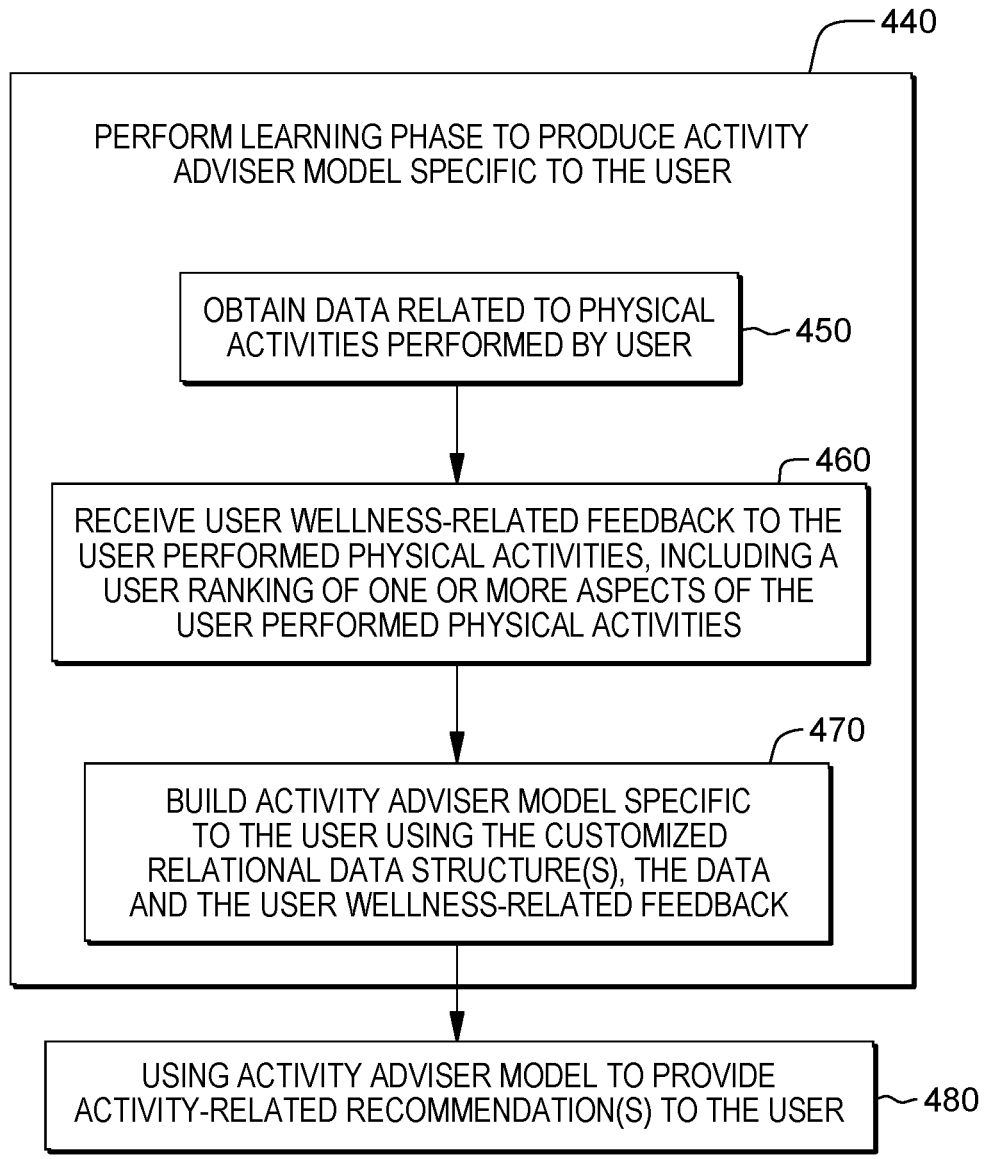

One embodiment of a process for building and using an activity adviser model in accordance with one or more aspects of the present invention, is depicted in FIGS. 4A & 4B.

Program code initially builds or accesses a body of domain knowledge 400 by accessing or receiving input from sources such as, for instance, online social applications, and in particular, physical activity training applications 401, as well as other available domain knowledge from other sources and/or one or more other adviser models 402.

Program code builds a relational data structure using cognitive analytics to learn from the body of domain knowledge 410. The relational data structure can, for instance, map different physical activities to different attributes, such as which food(s) consumed before, during, and/or after which yielded the best results, how many calories other user performing a particular physical activity burn, what is the average heart rate during a physical activity, what is the typical feedback (negative versus positive) that other users give to this physical activity, etc.

In an initial setup phase, program code receives a user profile 420, which includes data about a particular user, such as fitness goals (e.g., weight loss goals, muscle gain goals, etc.), health or medical restrictions (e.g., heart rate limit, blood sugar levels, physical limitations, etc.) as well as any other appropriate user information, such as age, fitness level, etc. In some embodiments, program code ranks and filters the relational data structure by comparing the attributes of, for instance, each physical activity found in the data structure derived from the body of knowledge, against the profile of the particular user. For instance, if the user has provided a profile indicating that the user has knee issues, the program code can rank activities such as running lower in the relational data structure, thus creating, a customized relational data structure specific to the user. Note that a variety of user profile data can be accounted for in this initial setup phase, and can be provided via one or more user devices coupled, for instance, via a network to the program code building the adviser model for the user and ultimately forming the recommendation engine, utilizing the activity adviser model for the user.

As illustrated in FIG. 4B, the program code next performs a learning phase to produce the activity adviser model specific to the user 440. This learning phase can include obtaining data relevant to physical activities performed by the user 450. For instance, program code can receive data obtained from one or more sensors associated with the user that track which exercises are performed by the user, where they are performed, a type and amount of calories consumed, for instance, before, during, and/or after the physical activity, etc.

Further, program code can receive user wellness-related feedback related to the user-performed physical activities, including a user ranking of one or more aspects of the user-performed physical activities 460. This user wellness-related feedback can also include data obtained from one or more sensors, or provided via one or more user devices, on additional parameters such as, for instance, heart rate, blood sugar level, amount of time of the physical activity, etc. Additionally, the user wellness-related feedback 460 can include a user ranking on each physical activity, such as, a rank from 1-10 on, for instance, how much the user enjoyed the physical activity, a rank of how easy it was for the user to perform to the physical activity, etc. Program code uses this user data to, in some embodiments, start an additional relational data structure that maps the user exercises and activities to yielded feedback/reaction of the user to activities performed.

Together the relational data structures can be used to build or used as the basis for the activity adviser model specific to the user 470. As part of building the model, program code can apply an algorithm to rank activities within one or more of the relational data structures to, for instance, "best overall" activities performed by the user. Similar to the training phase, this additional relational data structure can also be filtered depending on whether or not the physical activities are, for instance, contrary to a fitness goal or a health restriction of the user.

After the learning phase is complete, the activity adviser model can be used to provide an activity-related recommendation to the user 480. In one or more embodiments, the activity adviser model can be provided in a continuous operational mode available for providing suggestions, either reactively or proactively, where feedback from the user, along with feeds from domain knowledge, are used to continually or dynamically update the relational data structure(s) used by the activity adviser model.

In some embodiments, the activity adviser model includes a set of relational data structures and/or cognitive algorithms that make up the activity adviser model. The adviser model is able to receive available domain data, such as data from available training applications, and apply this knowledge to enhance a user's set of activities. The model accomplishes this task by creating, in one or more implementations, a set of ranked data structures (e.g., mapping physical activities to yielded results) and comparing them to one or more other set of ranked data structures (e.g., mapping physical activities to user preferences) to be able to provide a proactive recommendation to the user or a reactive recommendation to the user. An example of a proactive recommendation is detecting by the program code that a user is underperforming during each 5K bike activity, by not being able to complete the activity most of the time, and receiving feedback that the user feels fatigued after the ride. The activity adviser model consults, for instance, the relational data structure(s), such as the customized relational data structure derived from the body of domain knowledge, and detects that most successful bike riders consume a 300 calorie food rich in carbohydrates before this particular activity, and so, the model provides a recommendation to the user with a meal suggestion. As an example of a reactive recommendation, a user could forward a picture of a pizza to the program code or recommendation engine, and ask the engine which activity they should perform to burn those amount of calories. The activity adviser model can consult the body of domain knowledge to see which activities have been most successfully paired to burning of those pizza calories, and it will cross-reference those activities with a list of user-preferred activities to find a best possible match. The adviser model also can consult a set of scheduled activities and personal goals for the user, and so, if the user is about to run a marathon, or if the user's goal is to gain weight, then no extra exercises would be needed to burn off the calories from the pizza.

In some embodiments, the program code, or recommendation engine incorporating the activity adviser model, has the ability to learn about a person's physical activity patterns, and suggest an activity schedule based on various inputs, such as calorie consumption limits, health/fitness goals (e.g., weight loss, building muscle, etc.), and health considerations (e.g., blood sugar levels, heart rate, physical disabilities, etc.). Further, the adviser model has the ability to receive feedback after each activity-related suggestion and to react by adapting the data structures and/or algorithms for future suggestions. Further, the adviser model has the ability to find patterns from routines shared from social communities and/or applications, and available domain knowledge (e.g., training applications, journals, books, etc.), and use this information to enhance the user-specific recommendations going forward.

Figure 5:
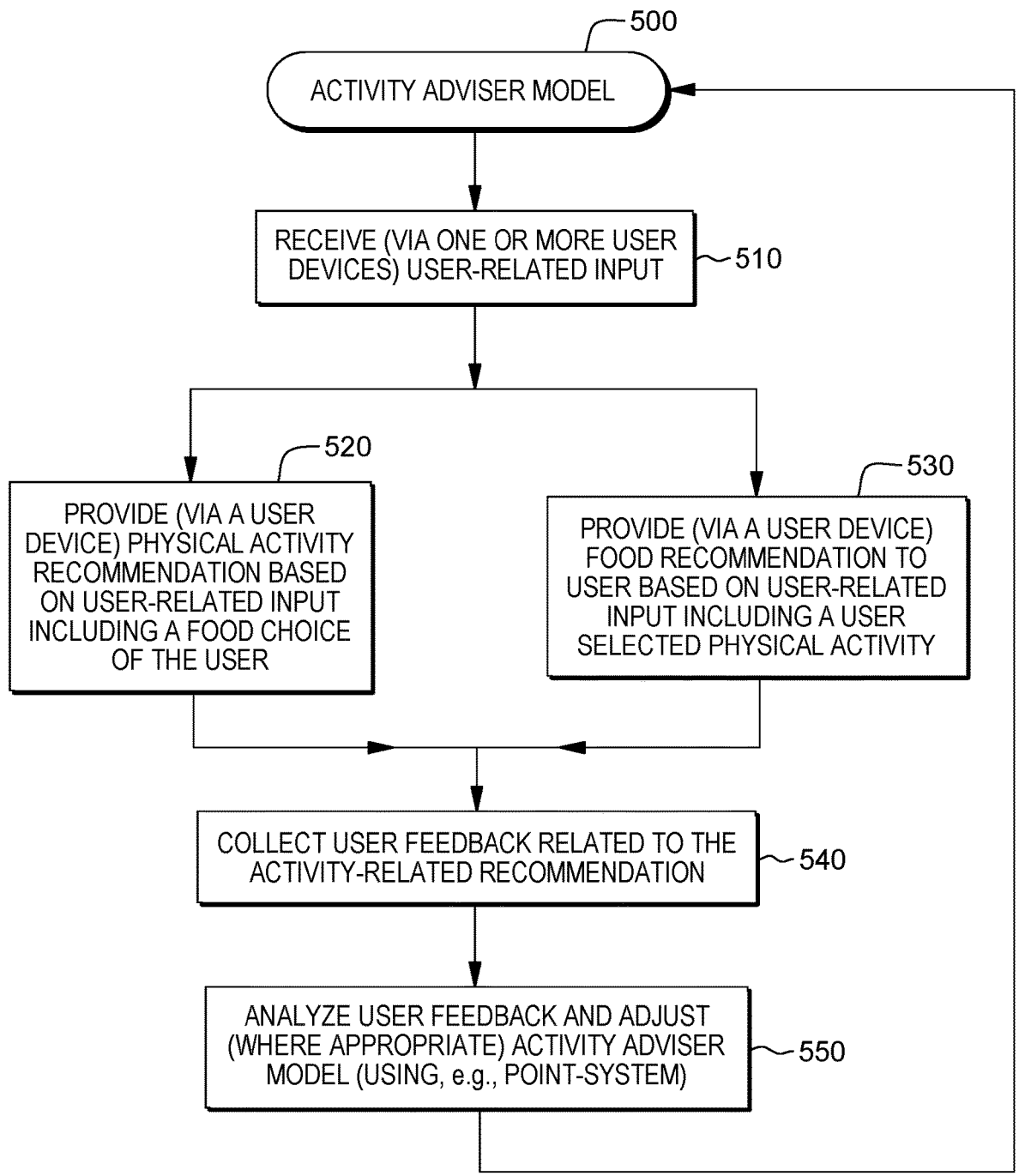
FIG. 5 depicts one embodiment of a process for using and updating an activity adviser model, in accordance with one or more aspects of the present invention.

FIG. 5 depicts one embodiment of operational use of an activity adviser model 500, in accordance with one or more aspects of the present invention. The activity adviser model receives, for instance, via one or more user devices or sensors, user-related input 510. As noted, the user-related input can be provided automatically, via one or more user IoT devices or sensors, or manually input by the user via one or more user devices, such as one or more mobile devices. Depending on the user-related input, the program code can, for instance, provide via a user device, a physical activity recommendation based on user-related input including a food choice of the user 520. Further, or alternatively, the program code can provide, via a user device, a food recommendation to the user based on user-related input, including a user-selected physical activity 530. Note in this regard that the food recommendation can be any food-related recommendation, such as a recommended number of calories, liquid intake recommendation, particular type of food, quantity of food, etc.

As noted, the activity adviser model 500 has the capability to continuously learn/refine the data structures and/or algorithms specific for the user so as to dynamically update the model specific to the user over time. To assist with this, user feedback is collected related to the activity-related recommendation (or fitness recommendation) 540. This feedback can include any appropriate user wellness-related feedback related to the user-performed physical activity and/or recommendation, such as described above. The program code analyzes the user feedback and adjusts (where appropriate) the activity adviser model using, for instance, a point or ranking system 550, such as described herein. The program code then returns to await receipt of further user-related input.

Figure 6:
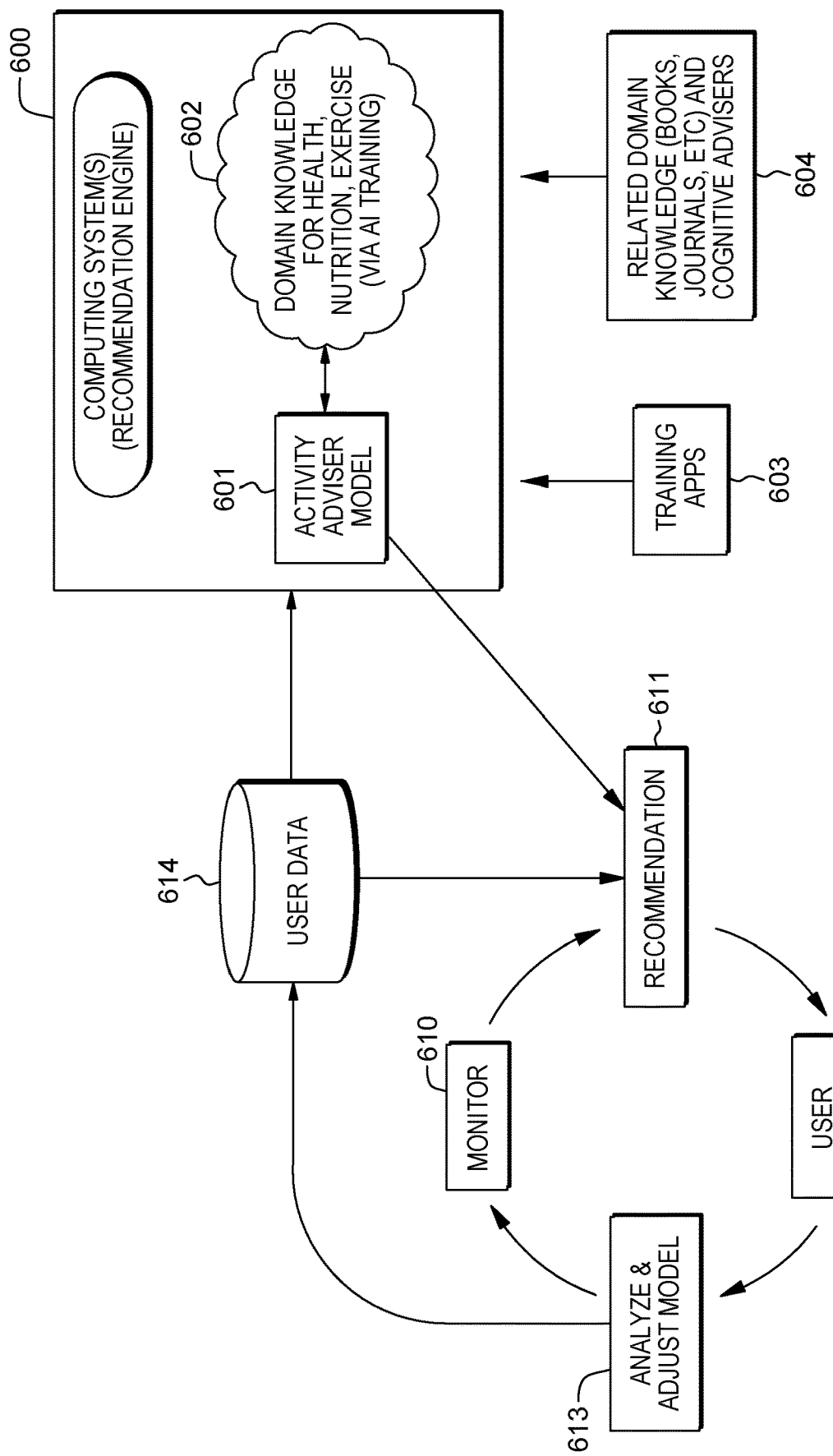
FIG. 6 depicts a further embodiment of a process of using and updating an activity adviser model, in accordance with one or more aspects of the present invention.

FIG. 6 is a further depiction of an exemplary interplay between the recommendation engine with the activity adviser model, the body of domain knowledge, as well as the user feedback provided through the user data structure to allow for dynamic updating of the activity adviser model for future recommendations. The recommendation engine 600 includes, in one or more embodiments, an activity adviser model 601 such as disclosed herein, along with access to a body of knowledge, such as domain knowledge for health, nutrition and exercise, which can be parsed via artificial intelligence and/or machine learning training 602 as described herein. As noted, any of a variety of sources can be accessed by the program code to produce and update the activity adviser model 601, including, online or social training applications 603, as well as related domain knowledge sources, such as books, journals, articles, etc., as well as potentially other activity adviser models 604.

The recommendation engine monitors for user-related input 610, which as noted, can be either automatic or manually input via a user device(s), and provide an activity-related or fitness-related recommendation 611 based thereon using the activity adviser model 601. Subsequent to the recommendation, the recommendation engine 600 receives user feedback related to the recommendation 612, such as the data and wellness-related feedback described above in connection with a physical activity performed by the user, as well as other data relevant to, for instance, a particular food recommendation for the user. The recommendation engine analyzes the user feedback and adjusts (where appropriate) the activity adviser model 613 by, for instance, updating the user data structure 614 and then using the information to update one or more relational data structures and/or algorithms of the activity adviser model 601.

A variety of modeling or algorithms can be used for providing reactive and/or proactive recommendations specific to a user, as described herein. For instance, during the learning phase, the cognitive activity adviser model can begin with a relational data structure that associates a variety of attributes or measurements to each type of physical activity or exercise. Note that the following specific description is by way of example only, and not by way of limitation. Other embodiments can use different parameters as input, as well as using different ranking scales that fit a particular limitation.

By way of example, the attributes or measurements can include for each activity one or more of:
 1. How many calories the physical activity burned.
 2. Using a 1-10 (too long—just the right amount) scale, the user rates how long the activity lasted.
 3. Using a 1-10 (sad—happy) scale, the user provides data on how the user felt before, during and/or after the exercise.
 4. How many calories (and which food items) were consumed by the user before, during and/or after the exercise.
 5. What was the range of heart rate during the exercise.
 6. What was the blood sugar level range after the exercise.
 7. Using a 1-10 (painful—painless) scale, the user describes a pain or difficulty level associated with the exercise.
 8. Using a 1-10 (not at all—really enjoyed) scale, the user describes how much the user enjoyed the exercise.
 9. Using a 1-10 (significant work—easy) scale, the user describes how easy it was to start the activity.

The data structure or table can initially rank activities using a point system. For instance, for items 2, 3, 7, 8 & 9 above, the scale can be directly converted into points. For instance, a "very easy to start" activity "10" answer for number 9 awards 10 points to the exercise or activity.

After the above initial ranking, then, for instance, items 5 & 6 (which are directly related to health inputs from the user) can be used to find out which exercises are putting the user at a health risk. These exercises could be moved to lower in the relational data structure, and can even be flagged as hazardous for the user. The activity adviser model can attempt to locate similar health profiles during a recommendation phase to identify if consuming a different set of calories (before, during and/or after the particular physical activity) can yield better results. For example, eating an energy bar during a run might help certain users be able to control sugar levels during or after the activity.

Items number 1 & 4 above can be analyzed together and directly mapped against, for instance, the user's specified fitness goals. The adviser model can assign between 1-10 (bad—good) points, depending upon how much a particular physical activity contributed to reaching the user's fitness goals. For example, a user who wants to lose weight and does an exercise that burns 1,000 calories, will be awarded 10 points, but if the same exercise causes the user to always consume 1,000 calories later, then it would be awarded less points.

Using the above approach, the activity adviser model can be built with a ranked list of physical activities, that the model can use each time user-related input is received by the recommendation engine, whether the user asks for input reactively, or when the adviser model proactively detects that, for instance, the user is not reaching a fitness goal or has encountered a health restriction.

In addition, as described herein, the activity adviser model can, in some embodiments, be linked to or access the body of domain knowledge, such as community-based domain knowledge, and in particular, fitness-related domain knowledge, such as fitness-related applications, to parse tips, food plans, training routines, and extract ideas on how to improve, for instance, lower ranked physical activities from the user. The adviser model can accomplish this by creating an additional table or structure which maps exercises to food consumed (e.g., before, during and/or after) that yielded the best results for other users. For instance, activity adviser model might learn that eating a salad before a run has been suggested by one or more other athletes as better than eating pizza (which is what the current user is doing) in terms of improving performance, and so, that information becomes a proactive recommendation for improvement. Similarly, the activity adviser model can synchronize with other activity adviser models on its network for related information, with the related information being provided or relevant geographically, by age, fitness goals, etc.

Those skilled in the art will recognize that numerous variations and extensions to the above-noted activity adviser model creation and recommendation process are possible.

Further exemplary embodiments of a computing environment to implement one or more aspects of the present invention are described below with reference to FIGS. 7-9.

By way of further example, FIG. 7 depicts one embodiment of a computing environment 700, which includes a computing system 712. Examples of well-known computing systems, environments, and/or configurations that may be suitable for use with computer system 712 include, but are not limited to, a server, a desktop computer, a work station, a wireless computer, a handheld or laptop computer or device, a mobile phone, a programmable consumer electronic device, a tablet, a personal digital assistant (PDA), and the like.

Computing system 712 can be described in the general context of computer system-executable instructions, such as program modules, being executed by a computer system. Generally, program modules include routines, programs, objects, components, logic, data structures, and so on that perform particular tasks or implement particular abstract data types.

As depicted in FIG. 7, computing system 712, is shown in the form of a general-purpose computing device. The components of computing system 712 can include, but are not limited to, one or more processors or processing units 716, a system memory 723, and a bus 718 that couples various system components including system memory 723 to processor 716.

In one embodiment, processor 716 may be based on the z/Architecture® offered by International Business Machines Corporation, or other architectures offered by International Business Machines Corporation or other companies. z/Architecture® is a registered trademark of International Business Machines Corporation, Armonk, N.Y., USA. One embodiment of the z/Architecture® is described in "z/Architecture Principles of Operation," IBM® Publication No. SA22-7832-11, 12th Edition, September 2017, which is hereby incorporated herein by reference in its entirety.

In other examples, it may be based on other architectures, such as the Power Architecture offered by International Business Machines Corporation. One embodiment of the Power Architecture is described in "Power ISA™ Version 2.07B," International Business Machines Corporation, Apr. 9, 2015, which is hereby incorporated herein by reference in its entirety. POWER ARCHITECTURE is a registered trademark of International Business Machines Corporation, Armonk, N.Y., USA. Other names used herein may be registered trademarks, trademarks, or product names of International Business Machines Corporation or other companies.

Bus 718 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing system 712 can include a variety of computer system readable media. Such media may be any available media that is accessible by computing system 712, and it includes both volatile and non-volatile media, removable and non-removable media.

System memory 723 can include computer system readable media in the form of volatile memory, such as random access memory (RAM) 730 and/or cache memory 732. Computing system 712 can further include other removable/non-removable, volatile/non-volatile computer system storage media. By way of example only, storage system 734 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media could be provided. In such instances, each can be connected to bus 718 by one or more data media interfaces. As described below, memory 723 can include at least one program product having a set (e.g., at least one) of program modules or code that are configured to carry out the functions of embodiments of the invention.

Program/utility 740, having a set (at least one) of program modules 742, can be stored in memory 732 by way of example, and not limitation, as well as an operating system, one or more application programs, other program modules, and program data. Each of the operating system, one or more application programs, other program modules, and program data or some combination thereof, can include an implementation of a networking environment. Program modules 742 generally carry out the functions and/or methodologies of embodiments of the invention as described herein. Alternatively, a recommendation engine processing module, logic, etc., 701 can be provided within computing environment 712 implementing and/or using an activity adviser model specific to a user as described herein.

Computing system 712 can also communicate with one or more external devices 714 such as a keyboard, a pointing device, a display 724, etc.; one or more devices that enable a user to interact with computing system 712; and/or any devices (e.g., network card, modem, etc.) that enable computing system 712 to communicate with one or more other computing devices. Such communication can occur via Input/Output (I/O) interfaces 722. Still yet, computing system 712 can communicate with one or more networks such as a local area network (LAN), a general wide area network (WAN), and/or a public network (e.g., the Internet) via network adapter 720. As depicted, network adapter 720 communicates with the other components of computing system, 712, via bus 718. It should be understood that although not shown, other hardware and/or software components could be used in conjunction with computing system 712. Examples, include, but are not limited to: microcode, device drivers, redundant processing units, external disk drive arrays, RAID systems, tape drives, and data archival storage systems, etc.

One or more aspects may relate to or use cloud computing.

It is understood in advance that although this disclosure includes a detailed description on cloud computing, implementation of certain teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

A cloud computing node can include a computer system/server, such as the one depicted in FIG. 7. Computer system/server 712 of FIG. 7 can be practiced in distributed cloud computing environments where tasks are performed by remote processing devices that are linked through a communications network. In a distributed cloud computing environment, program modules may be located in both local and remote computer system storage media including memory storage devices. Computer system/server 712 is capable of being implemented and/or performing any of the functionality set forth hereinabove.

Figure 8:
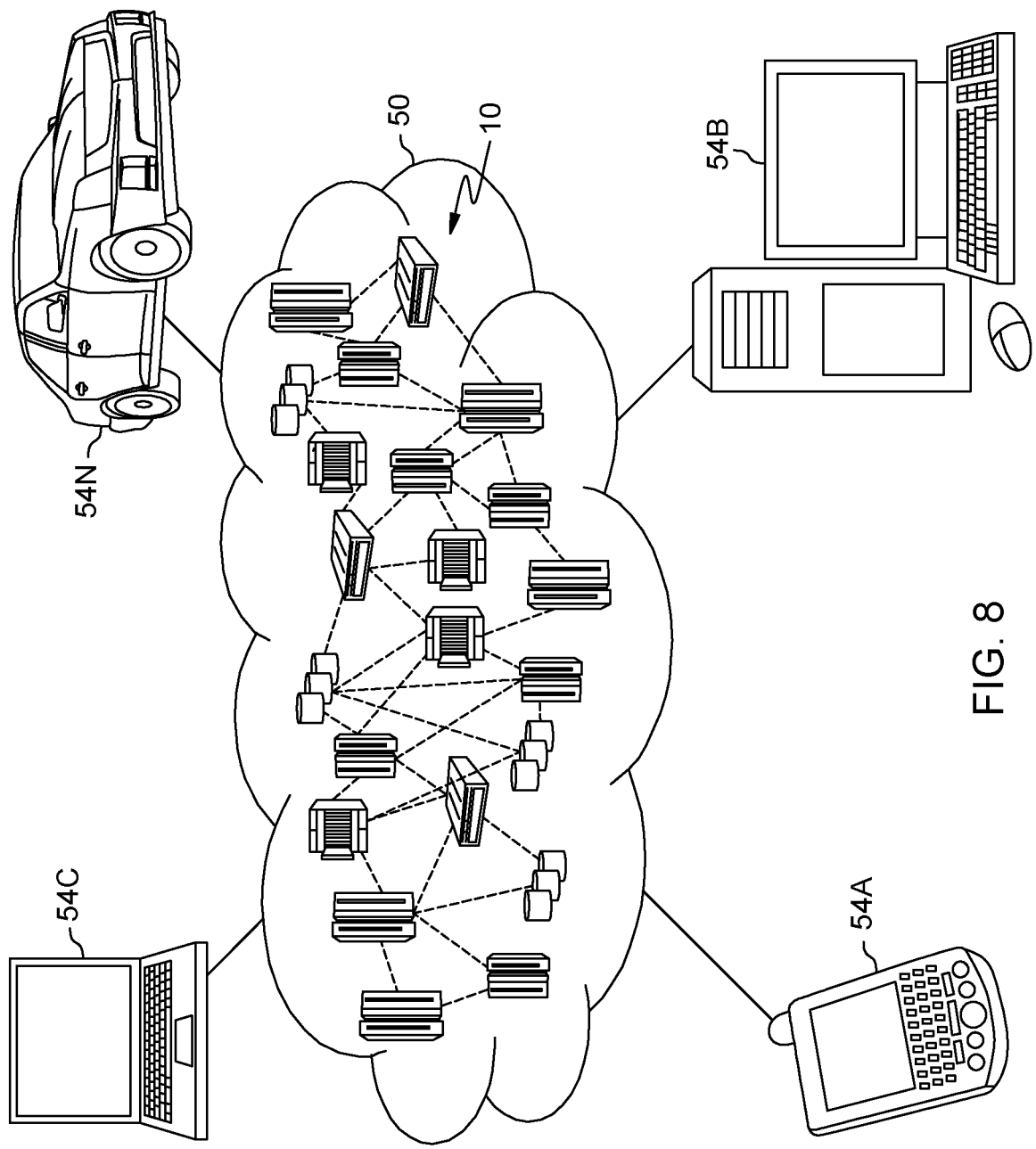
FIG. 8 depicts one embodiment of a cloud computing environment which can facilitate implementing, or be used in association with, one or more aspects of the present invention.

Referring now to FIG. 8, illustrative cloud computing environment 50 is depicted. As shown, cloud computing environment 50 can comprise one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 9:
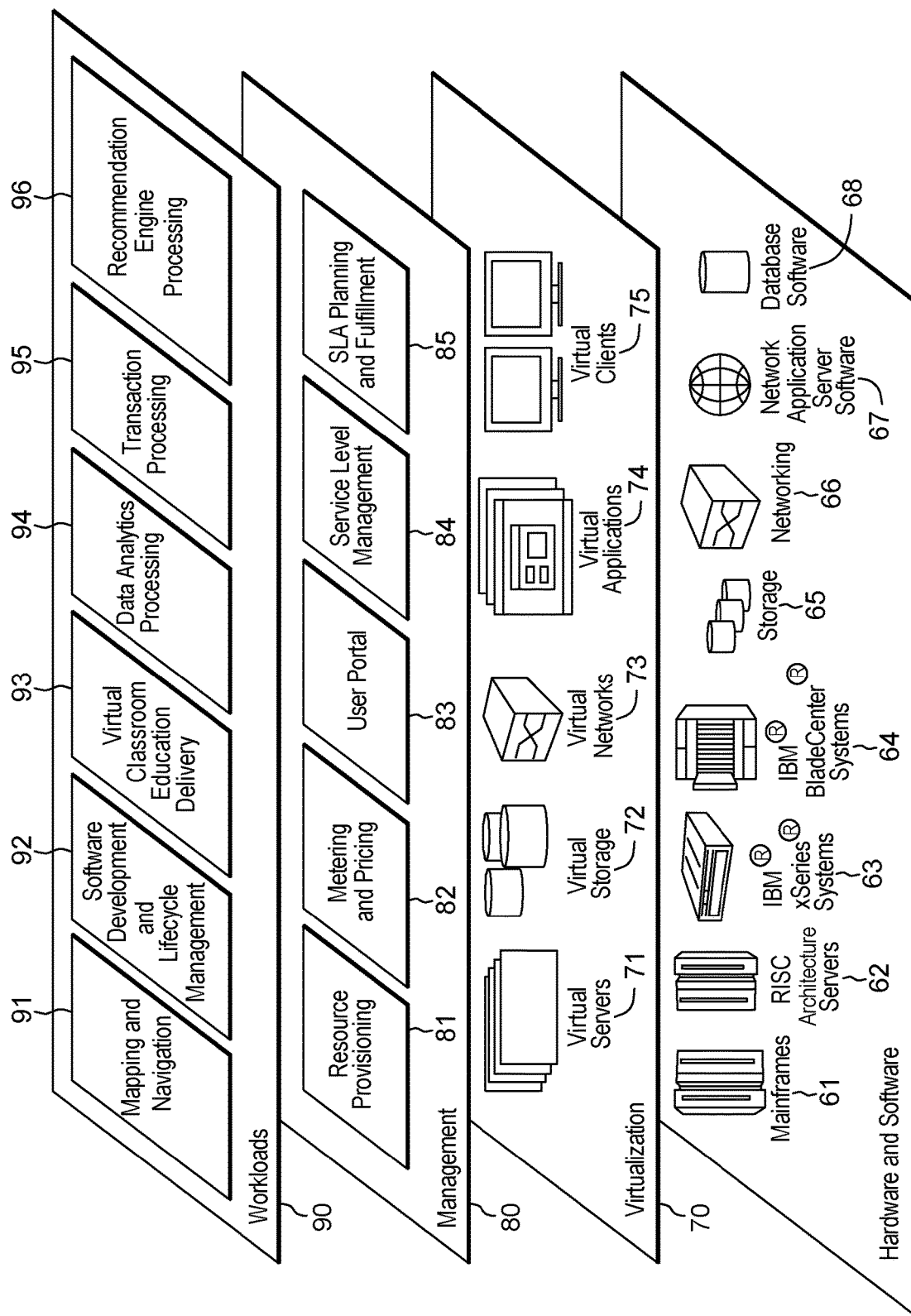
FIG. 9 depicts an example of abstraction model layers, which can facilitate implementing recommendation engine processing, in accordance with one or more aspects of the present invention.

Referring to FIG. 9, a set of functional abstraction layers provided by cloud computing environment 50 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and recommendation engine processing 96.

The descriptions of the various embodiments of the present invention have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The present invention may be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In addition to the above, one or more aspects may be provided, offered, deployed, managed, serviced, etc. by a service provider who offers management of customer environments. For instance, the service provider can create, maintain, support, etc. computer code and/or a computer infrastructure that performs one or more aspects for one or more customers. In return, the service provider may receive payment from the customer under a subscription and/or fee agreement, as examples. Additionally or alternatively, the service provider may receive payment from the sale of advertising content to one or more third parties.

In one aspect, an application may be deployed for performing one or more embodiments. As one example, the deploying of an application comprises providing computer infrastructure operable to perform one or more embodiments.

As a further aspect, a computing infrastructure may be deployed comprising integrating computer readable code into a computing system, in which the code in combination with the computing system is capable of performing one or more embodiments.

As yet a further aspect, a process for integrating computing infrastructure comprising integrating computer readable code into a computer system may be provided. The computer system comprises a computer readable medium, in which the computer medium comprises one or more embodiments. The code in combination with the computer system is capable of performing one or more embodiments.

Although various embodiments are described above, these are only examples. For example, computing environments of other architectures can be used to incorporate and use one or more embodiments. Further, different instructions, instruction formats, instruction fields and/or instruction values may be used. Many variations are possible.

Further, other types of computing environments can benefit and be used. As an example, a data processing system suitable for storing and/or executing program code is usable that includes at least two processors coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A method, comprising:
   receiving, by one or more processors, user profile data of a user to facilitate generating a custom machine learning model specific to the user to provide activity-related recommendations specific to the user;
   ranking, by the one or more processors, physical activity data in a relational data structure, at least in part, based on the user profile data to create a customized relational data structure of ranked physical activities for the user to facilitate generating the custom machine learning model specific to the user to provide activity-related recommendations specific to the user, the relational data structure mapping physical activities to one or more associated attributes;
   generating the custom machine learning model specific to the user to provide activity-related recommendations specific to the user, the generating comprising:
   obtaining sensor data related to physical activities performed by the user from one or more sensors proximate to the user;
   receiving user wellness-related feedback data related to the user-performed physical activities, the user wellness-related feedback data including a user ranking of one or more aspects of the user-performed physical activities; and
   generating the custom machine learning model specific to the user using the customized relational data structure, the sensor data and the user wellness-related feedback data, the custom machine learning model being generated to provide the activity-related recommendations specific to the user; and
   using, by the one or more processors, the custom machine learning model specific to the user to provide an activity-related recommendation specific to the user.

2. The method of claim 1, wherein the activity-related recommendation of the generated custom machine learning model specific to the user is selected from the group consisting of: a physical activity to be performed by the user based on a food choice of the user, and a food to be consumed by the user based on a physical activity choice of the user.

3. The method of claim 1, wherein the generated custom machine learning model specific to the user relates, at least in part, ranked physical activities for the user to recommended food consumption for the ranked physical activities.

4. The method of claim 1, further comprising:
   generating, by the one or more processors, the relational data structure that maps physical activities to one or more associated attributes, the generating being based on a body of domain knowledge data obtained from a plurality of online sources; and
   wherein generating the relational data structure comprises cognitively analyzing, by the one or more processors, the body of domain knowledge data obtained from the plurality of online sources to build the relational data structure.

5. The method of claim 4, wherein the cognitively analyzing extracts from the body of domain knowledge data obtained from the plurality of online sources a recommended food and time of consumption for a physical activity of the relational data structure, the time of consumption being selected from the group consisting of: a time before the physical activity, a time during the physical activity, and a time after the physical activity.

6. The method of claim 4, wherein the body of domain knowledge data obtained from the plurality of online sources comprises one or more training application-based sources and one or more other online sources relating, at least in part, physical activity and food consumption.

7. The method of claim 1, wherein the user profile data comprises user input data, the user input data being selected from the group consisting of user goal data and user health restrictions data, and wherein the ranking of the physical activities in the relational data structure is based, at least in part, on the user input data.

8. The method of claim 1, wherein the sensor data obtained related to the physical activities performed by the user is selected from the group consisting of: user physiological sensor data, user heart rate sensor data, user blood pressure sensor data, user blood oxygen saturation sensor data, and user temperature sensor data, and the sensor data is obtained before, during, or after one or more of the physical activities.

9. The method of claim 1, wherein the user wellness-related feedback data includes user data ranking multiple aspects of a user-performed physical activity based on user perception, the user data ranking the multiple aspects including at least some of: user data ranking of length of the physical activity, user data ranking how the user feels during the physical activity, user data ranking user enjoyment of the physical activity, and user data ranking of ease of the physical activity to the user.

10. The method of claim 1, wherein the user wellness-related feedback data includes user-provided data on food consumed by the user in association with a physical activity of the physical activities performed by the user.

11. The method of claim 1, further comprising dynamically updating over time the custom machine learning model based on new data, the new data being selected from the group consisting of: one or more updates to a body of domain knowledge data used to build the relational data structure to be customized for the user, further sensor data obtained related to further physical activities performed by the user from the one or more sensors proximate to the user, and further user wellness-related feedback data received from the user related to the further user-performed physical activities.

12. The method of claim 1, further comprising dynamically updating the generated custom machine learning model specific to the user over time, the dynamically updating being based, at least in part, on additional user wellness-related feedback data related to the user performing one or more physical activities of the physical activities, the additional user wellness-related feedback data including, at least in part, a re-ranking of one or more aspects of the user-performed one or more physical activities.

13. A computer system comprising:
a memory; and
a processor in communication with the memory, wherein the computer system is configured to perform a method comprising:
receiving, by one or more processors, user profile data of a user to facilitate generating a custom machine learning model specific to the user to provide activity-related recommendations specific to the user;
ranking, by the one or more processors, physical activity data in a relational data structure, at least in part, based on the user profile data to create a customized relational data structure of ranked physical activities for the user to facilitate generating the custom machine learning model specific to the user to provide activity-related recommendations specific to the user, the relational data structure mapping physical activities to one or more associated attributes;
generating the custom machine learning model specific to the user to provide activity-related recommendations specific to the user, the generating comprising:
obtaining sensor data related to physical activities performed by the user from one or more sensors proximate to the user;
receiving user wellness-related feedback data related to the user-performed physical activities, the user wellness-related feedback data including a user ranking of one or more aspects of the user-performed physical activities; and
generating the custom machine learning model specific to the user using the customized relational data structure, the sensor data and the user wellness-related feedback data, the custom machine learning model being generated to provide the activity-related recommendations specific to the user; and
using, by the one or more processors, the custom machine learning model specific to the user to provide an activity-related recommendation specific to the user.

14. The computer system of claim 13, wherein the activity-related recommendation of the generated custom machine learning model specific to the user is selected from the group consisting of: a physical activity to be performed by the user based on a food choice of the user, and a food to be consumed by the user based on a physical activity choice of the user.

15. The computer system of claim 13, wherein the generated custom machine learning model specific to the user relates, at least in part, ranked physical activities for the user to recommended food consumption for the ranked physical activities.

16. The computer system of claim 13, further comprising dynamically updating over time the generated custom machine learning model based on new data, the new data being selected from the group consisting of: one or more updates to a body of domain knowledge data used to build the relational data structure to be customized for the user, further sensor data obtained related to further physical activities performed by the user from the one or more sensors proximate to the user, and further user wellness-related feedback data received from the user related to the further user-performed physical activities.

17. The computer system of claim 13, further comprising dynamically updating the generated custom machine learning model specific to the user over time, the dynamically updating being based, at least in part, on additional user wellness-related feedback data related to the user performing one or more physical activities of the physical activities, the additional user wellness-related feedback data including, at least in part, a re-ranking of one or more aspects of the user-performed one or more physical activities.

18. A computer program product comprising:
a computer-readable storage medium readable by a processing circuit and storing instructions for execution by the processing circuit for performing a method comprising:
receiving, by one or more processors, user profile data of a user to facilitate generating a custom machine learning model specific to the user to provide activity-related recommendations specific to the user;
ranking, by the one or more processors, physical activity data in a relational data structure, at least in part, based on the user profile data to create a customized relational data structure of ranked physical activities for the user to facilitate generating the custom machine learning model specific to the user to provide activity-related recommendations specific to the user, the relational data structure mapping physical activities to one or more associated attributes;
generating the custom machine learning model specific to the user to provide activity-related recommendations specific to the user, the generating comprising:
obtaining sensor data related to physical activities performed by the user from one or more sensors proximate to the user;
receiving user wellness-related feedback data related to the user-performed physical activities, the user wellness-related feedback data including a user ranking of one or more aspects of the user-performed physical activities; and
generating the custom machine learning model specific to the user using the customized relational data structure, the sensor data and the user wellness-related feedback data, the custom machine learning model being generated to provide the activity-related recommendations specific to the user; and using, by the one or more processors, the custom machine learning model specific to the user to provide an activity-related recommendation specific to the user.

19. The computer program product of claim 18, wherein the activity-related recommendation of the generated custom machine learning model specific to the user is selected from the group consisting of: a physical activity to be performed by the user based on a food choice of the user, and a food to be consumed by the user based on a physical activity choice of the user.

20. The computer program product of claim 18, wherein the generated custom machine learning model specific to the user relates, at least in part, ranked physical activities for the user to recommended food consumption for the ranked physical activities.

* * * * *